United States Patent [19]

Grane et al.

[11] 4,239,926
[45] Dec. 16, 1980

[54] REMOVING WATER FROM TERTIARY BUTYL ALCOHOL

[75] Inventors: Henry R. Grane, Springfield; John C. Jubin, Jr., Wallingford; G. Richard Worrell, Media, all of Pa.

[73] Assignee: Atlantic Richfield Company, Los Angeles, Calif.

[21] Appl. No.: 51,561

[22] Filed: Jun. 25, 1979

[51] Int. Cl.³ .................. B01D 3/40; C07C 29/30
[52] U.S. Cl. .................. 568/910; 203/18; 203/44; 203/69; 203/74; 203/75; 203/78; 203/DIG. 13
[58] Field of Search ............... 568/916; 203/18, 69, 203/43–46, 95, 53, 74, 75, 76, 77, 78, 79, 80, 81–85, 39, DIG. 13; 44/56

[56] References Cited

U.S. PATENT DOCUMENTS

| 1,950,889 | 3/1934 | Hartman | 568/916 |
|---|---|---|---|
| 2,537,115 | 1/1951 | Scheibel | 203/69 |
| 2,591,672 | 4/1952 | Catterall | 203/18 |
| 2,751,337 | 6/1956 | Goddin et al. | 203/96 |

FOREIGN PATENT DOCUMENTS 525258  5/1956  Canada ............................ 203/18

*Primary Examiner*—Wilbur L. Bascomb, Jr.
*Attorney, Agent, or Firm*—John R. Ewbank

[57] ABSTRACT

Isobutane is oxidized to provide a debutanized oxidate comprising tertiary butyl alcohol, acetone, water and other byproducts including high boiling products. Water is removed by extractive distillation using a combination of water and xylene as the extractant. The molar amount of recycled water is greater than the amount of water to be removed from the oxidate. By thus recirculating water through the decantation zone the acetone is satisfactorily coextracted from the butyl alcohol in such a manner that a stream of acetone and a stream of water, as well as the desired dry stream of tertiary butyl alcohol can be withdrawn. If the water is not recycled, the acetone will concentrate in the upper section of the distillation zone and reduce the volatility of water, thereby inhibiting the water removal from the tertiary butyl alcohol.

6 Claims, 1 Drawing Figure

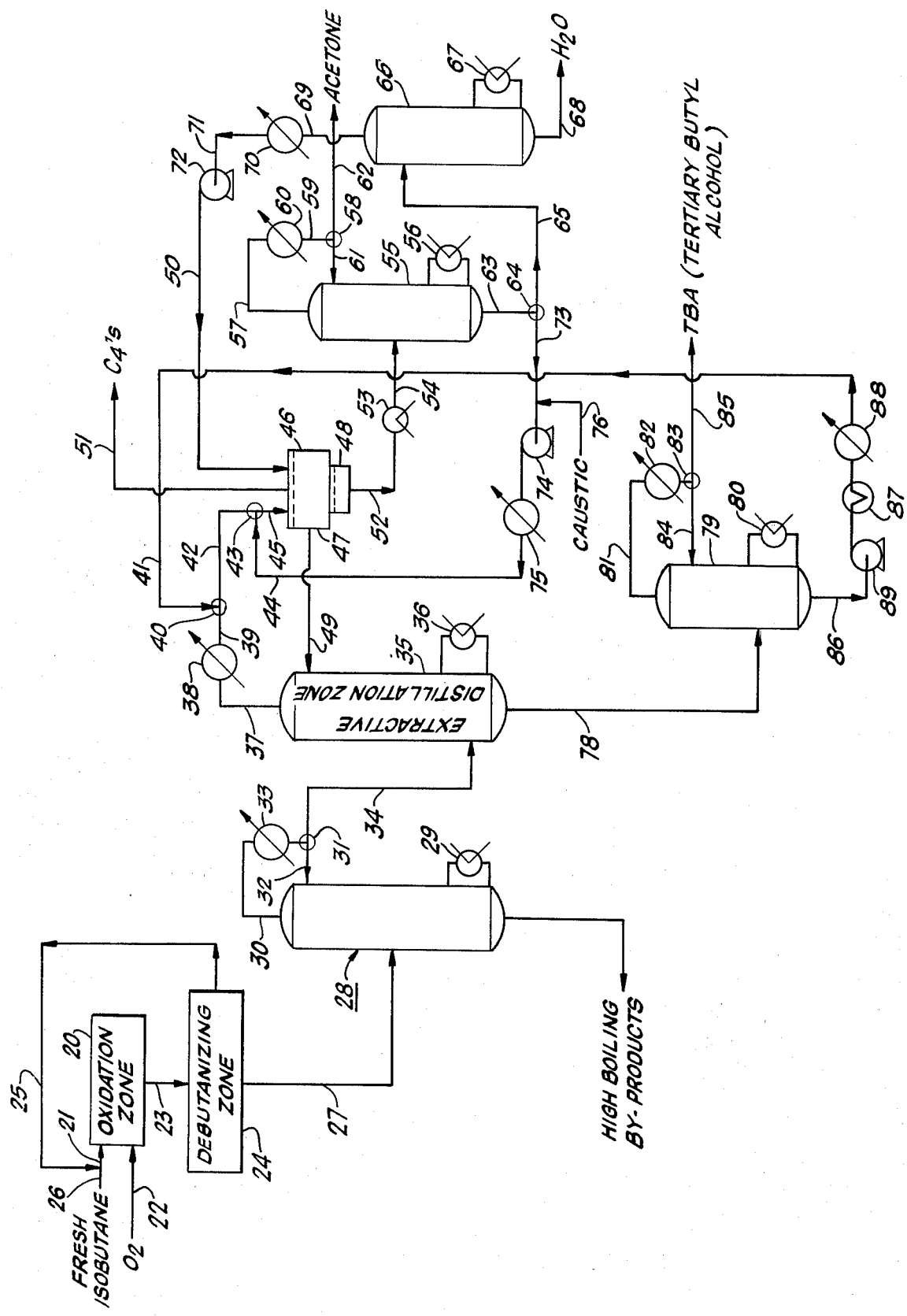

REMOVING WATER FROM TERTIARY BUTYL ALCOHOL

RELATED APPLICATIONS

Reference is made to the applications of Henry R. Grane, John C. Jubin, Jr. and G. Richard Worrell concerning similar subject matter, all the disclosures of which are deemed here reiterated and incorporated herein, said applications including "Oxygen-Containing Fuels" Ser. No. 045,454, filed: June 4, 1979 and "Manufacture of Tertiary Butyl Alcohol" Ser. No. 045,365, filed: June 4, 1979.

BACKGROUND OF INVENTION

This invention relates to the drying of tertiary butyl alcohol by extractive distillation using as an extractant a composition comprising xylene.

PRIOR ART

Extractive distillation has heretofore been employed in drying of liquids. Because tertiary butyl alcohol and water form a primary azeotrope boiling at 176° F., which is below the 181° F. boiling point of tertiary butyl alcohol, it is feasible to prepare a fraction featuring dry tertiary butyl alcohol if the water content of the initial tertiary butyl alcohol is only a small fraction of the 11.7 weight percent (35.4 mol percent) water content of such azeotrope. There is a demand for a method of manufacturing tertiary butyl alcohol so that it contains less than about 1.5% water. The principal use for tertiary butyl alcohol is as a component contributing high octane to gasoline. Moreover the tertiary butyl alcohol is an anti-icing agent in the gasoline. Although there are possibilities for drastically drying tertiary butyl alcohol (TBA) by use of molecular sieves or other sorptive agents, the market demand has been primarily for tertiary butyl alcohol sufficiently dried to contain less than about 1.5 weight percent of water.

SUMMARY OF THE INVENTION

In accordance with the present invention TBA is dried by extractive distillation with an extractant using recycled xylene. More mols of water are recirculated through a decantation zone per hour than the mols of water withdrawn from the drying process per hour. A stream of acetone as well as the streams of water and the stream of TBA are withdrawn from the process.

DESCRIPTION OF FLOWSHEET

In the accompanying drawings, FIG. 1 is a schematic flowsheet of a process embodying the present invention.

DESCRIPTION OF EMBODIMENT

In the embodiment shown in the flowsheet, an oxidation zone 20 is supplied with a stream of isobutane 21 and a stream of an oxygen-containing gas 22. A stream of reaction mixture 23 is directed to a debutanizing zone 24 from which a recycle isobutane stream 25 is directed back for blending to be a part of total isobutane stream 21 after mixing with fresh isobutane 26.

From the debutanizing zone an oxidate stream 27 is directed to a preliminary distillation zone 28. Reboiler 29 maintains a lower proportion of such preliminary distillation zone at a controlled temperature in the range from about 230° F. to about 250° F., such as 240° F. The preliminary distillation zone is maintained at about 20 lbs. per square inch gauge. An overhead stream 30 is directed to a condenser 33 and thence to a divider 31 for controlling the reflux ratio.

The reflux ratio may be controlled at about 0.3 parts of reflux per one part of withdrawn overhead. Such reflux can be directed back to the distillation zone 28 through stream 32. A principal portion of the overhead is directed as a feed stream 34 to extractive distillation zone 35. A reboiler 36 maintains an appropriate temperature near the bottom of the extractive distillation zone 35. Such temperature may be within a range from about 280° to about 300°, such as 290°. The extractive distillation zone 35 can be maintained at a pressure of about 15 psig. An overhead stream 37 from the extractive distillation zone 35 can be condensed by heat exchanger 38 and can flow through stream 39 to a merging zone 40. A recycle stream 41 consisting predominantly of recycled xylene merges with the condensate stream 39 in merging zone 40 to provide a xylene stream 42 which goes to a washing zone 43. An aqueous recycle stream 44 also goes to washing zone 43 from which is withdrawn a turbulent stream 45 in which acetone is extracted from the xylene into the water. A dilute acetone solution is recycled to decantation zone 46 through line 50. A decantation zone 46 permits the separation of the mixture into an upper xylene layer 47 and a lower aqueous layer 48. Most of the acetone is in the aqueous layer 48, thereby preventing the propensity of acetone vapor to fill the vapor portions of the upper part of extractive distillation zone 35. An extractant stream 49 directs the extractant at a controlled rate from decantation zone 46 to the extractive distillation zone 35. The decantation zone 46 is maintained at an appropriate temperature within the range of about 40° to 120° F., such as 100° F. Because minor amounts of $C_4$ hydrocarbon can occur in the oxidate stream 27, a $C_4$ hydrocarbon vapor withdrawal line 51 is provided at the decantation zone 46. A dilute solution of acetone is withdrawn from the aqueous layer 48 through line 52, heat exchanger 53, and feed stream 54 to an acetone stripping distillation zone 55. A reboiler 56 heats the liquid in the lower portion of acetone stripping distillation zone 55. An overhead stream 57 flows through a condenser 60 to a reflux control system 58 which directs an acetone stream 61 as reflux to the acetone stripping distillation zone 55. Acetone is withdrawn through overhead 57, condenser 60, control 58, and line 62. From the bottom of acetone stripping distillation zone 55 there is withdrawn a stream 63 directed to a divider 64 so that a small portion of the bottom stream can be directed as stream 65 to water stripping distillation zone 66. A reboiler 67 maintains a controlled temperature in the bottom of water stripping distillation zone 66. The stream of water 68 withdrawn as bottoms from the water stripping distillation zone 66 corresponds generally to the water formed in the oxidation zone 20 as a byproduct from the oxidation of the isobutane. Such water stream 68 also contains sodium formate and/or other salts formed in the process. An overhead stream 69 from water stripping distillation zone 66 is directed through a condenser 70 to provide a dilute acetone solution stream 71 which is recirculated to the decantation zone 46 through pump 72 and recycle stream 50.

Particular attention is directed to the unusual feature of the present invention whereby the recycled water stream 44 has a flow rate greater than the byproduct water stream 68. The extractive distillation step is conducted for the purpose of drying the tertiary butyl alcohol. It is surprising that the amount of water employed on a recirculating basis is greater than the amount of water to be withdrawn as byproduct. It is oftentimes advantageous to maintain a recycle rate which is about 150% to about 400% of the water withdrawal rate. For example, the recirculation rate can be 250% of the water withdrawal rate. From divider 64 an aqueous stream 73 can be directed to a pump 74 and through a heat exchanger 75 to the water recirculation line 44. An alkali injection jet 76 adds sufficient sodium hydroxide to the recirculated water to promote the formation of sodium formate and methanol from the methyl formate encountered in the washing zone 43.

It should be especially noted that as the oxidate vapor passes upwardly in the extractive distillation zone 35, the tertiary butyl alcohol is selectively extracted and the water, acetone, methyl formate, methanol, isobutane, and miscellaneous byproducts which are more volatile than tertiary butyl alcohol are selectively advanced towards overhead stream 37. The water content of the oxidate is thus advanced selectively toward overhead stream 37 so that the tertiary butyl alcohol is dried by extractive distillation. The extraction of acetone from the xylene can proceed smoothly in washing zone 43 because the recycle water is about 250% of the withdrawn water. Because of the alkali injected at jet 76, the trace amounts of methyl formate and tertiary butyl formate in the oxidate can be hydrolyzed in washing zone 43 to liberate the tertiary butyl alcohol and methanol and to form a very minor amount of sodium formate, which tends to be extracted into the aqueous phase 48 and thence to be withdrawn with the product water stream 68.

The ratio of water to acetone in the debutanized oxidate can vary in response to the selectivity and severity of oxidation conditions. Ordinarily the unit mol ratio of water to acetone can be within the range from about 0.5 to 9, such as 3.

From the bottom of the extractive distillation zone 35 a stream 78 is directed to xylene stripping distillation zone 79. A reboiler 80 heats the lower portion of xylene stripping distillation zone 79 so that an overhead stream 81 is directed through a condenser 82 to a reflux control zone 83. It is usually satisfactory to maintain a reflux ratio of about 1:1 so that there is about 1 volume of tertiary butyl alcohol being directed back toward the distillation zone 79 through line 84 and about 1 volume of tertiary butyl alcohol being withdrawn as the principal product of the process through line 85. Thus, it is a process for the drying of tertiary butyl alcohol by the removal of water from oxidate. Such drying is accomplished by reason of the use of xylene as the extractant in an extractive distillation process. By recycling water through washing zone 43 at a rate greater than the rate of withdrawn water, the extractive distillation process is effective notwithstanding the presence of acetone, methyl formate, and other volatile oxygen-containing organic compounds in the oxidate. If the water is not recycled, the acetone will concentrate in the upper section of the distillation zone and reduce the volatility of water, thereby inhibiting the water removal from the tertiary butyl alcohol.

From the bottom of the xylene distillation zone 79 is withdrawn a xylene stream 86 which is directed to a xylene recycle stream 41. A pump 89 is ordinarily included in the path from the distillation zone 79 to the mixing zone 40. Heat exchangers 87 and 88 may be included in such path or heat exchangers 53, 56, and/or other heat exchangers may be substituted by routine engineering in response to heat loading.

The invention is further clarified by noting that it concerns a method in which oxygen reacts with isobutane in an isobutane oxidation zone to provide tertiary butyl alcohol as a principal product and in which water is amont the byproducts, and in which the tertiary butyl alcohol is employed for blending into gasoline, thus necessitating a smaller amount of water in the tertiary butyl alcohol than formed as a byproduct from the oxidation of isobutane, the improvement in drying the tertiary butyl alcohol which consists of directing a stream of wet tertiary butyl alcohol into an extractive distillation zone, and directing a stream of xylene downwardly through said extractive distillation zone while vaporizing a major portion of the water from the tertiary butyl alcohol, and withdrawing overhead vapors of water and other volatilized components, transferring from the bottom of said extractive distillation zone a liquid stream comprising xylene and tertiary butyl alcohol to the middle of a distillation zone designated as a xylene stripping zone, and removing from the bottom of said xylene stripping zone a stream of recyclable xylene and withdrawing overhead from said xylene stripping zone a stream of vapor of substantially dry tertiary butyl alcohol.

Various modifications of the invention are possible without departing from the scope of the invention as set forth in the appended claims.

We claim:

1. In the method in which oxygen reacts with isobutane in an isobutane oxidation zone to provide tertiary butyl alcohol as a principal product and in which water is among the byproducts, and in which the tertiary butyl alcohol is employed for blending into gasoline, thus necessitating a smaller amount of water in the tertiary butyl alcohol than formed as a byproduct from the oxidation of isobutane, the improvement in drying the tertiary butyl alcohol which consists of:
   directing a stream of wet tertiary butyl alcohol into an extractive distillation zone, and directing a stream of xylene downwardly through said extractive distillation zone while vaporizing a major portion of the water from the tertiary butyl alcohol, and withdrawing overhead vapors of water and other volatilized components;
   transferring from the bottom of said extractive distillation zone a liquid stream comprising xylene and tertiary butyl alcohol to the middle of a distillation zone designated as a xylene stripping zone, and removing from the bottom of said xylene stripping zone a stream of recyclable xylene, and withdrawing overhead from said xylene stripping zone a stream of vapor of substantially dry tertiary butyl alcohol.

2. The method of claim 1 in which a stream comprising TBA, acetone, water, and high boiling components are directed from said isobutane oxidation zone and fed to a preliminary distillation zone at a controlled molar rate, and a bottoms stream comprising high boiling components having at about 20 psig a boiling point above about 240° F. is withdrawn at a rate which is at a small fraction of the molar rate at which said stream comprising TBA is fed, the stream other than said high boiling products advancing overhead from said preliminary distillation zone as a stream of wet tertiary butyl alcohol toward said extractive distillation zone.

3. The method of claim 1 in which said stream of wet tertiary butyl alcohol contains acetone, and is fed to said extractive distillation zone at a controlled molar rate at a pressure of about 15 psig, and said stream of recyclable xylene is directed downwardly through said extractive distillation zone at a rate which is from about 75% to 90% of the molar rate at which said stream of wet tertiary butyl alcohol is fet to said extractive distillation zone, the bottoms of said extractive distillation zone being maintained at a temperature within a range from about 280° F. to about 300° F., and the overhead from said extractive distillation zone is condensed and directed to a washing zone and thence to a decanting zone maintained at a temperature within the range from about 50° F. to about 110° F., said washing zone effectively extracting a major portion of the acetone into an aqueous layer, said washing zone featuring the recycling through the washing zone of a molar quantity of recycled water which is about 150% to 400% of the molar quantity of water in said stream of wet tertiary butyl alcohol, said decanting zone comprising an upper layer of recyclable xylene and a lower aqueous layer comprising acetone, the recyclable xylene being directed from said decanting zone to an upper portion of said extractive distillation zone.

4. The method of claim 1 in which a stream comprising TBA and xylene is directed at a controlled rate to said xylene stripping zone maintained at about 10 psig, and TBA is withdrawn as an overhead stream, and the lower portion of said xylene stripping zone is maintained at a temperature within a range from about 290° F. to about 310° F., and a bottoms stream of recyclable xylene is advanced therefrom, and the reflux ratio of the condensed TBA is maintained near one volume of TBA directed to the upper portion of said xylene stripping zone per one volume of TBA withdrawn.

5. The method of claim 3 in which an aqueous stream comprising acetone is directed from a lower layer of said decanting zone to an acetone stripping distillation zone, from which is withdrawn overhead a stream of acetone, and a bottoms stream from said acetone stripping distillation zone is divided so that a major portion of recirculated to said washing zone, and a minor portion is directed to a water stripping distillation zone from the bottom of which is withdrawn a stream of water, said major portion being from about 150% to about 400% of said minor portion of water, and the distillation overhead from said water stripping distillation zone is directed to said decanting zone.

6. In the method in which oxygen reacts with isobutane in an isobutane oxidation zone to provide tertiary butyl alcohol as a principal product and in which water is among the byproducts, the improvement in drying the tertiary butyl alcohol which consists of:

directing from said isobutane oxidation zone a feed stream comprising TBA, acetone, water, and high boiling components to a preliminary distillation zone at a controlled molar rate, and withdrawing a bottoms stream comprising high boiling components at a rate which is at a small fraction of the molar rate at which said stream comprising TBA is fed, said high boiling components having at about 20 psig a boiling point above about 240° F., the stream other than said high boiling products advancing overhead from said preliminary distillation zone as a stream of wet tertiary butyl alcohol, directing said stream of wet tertiary butyl alcohol to an extractive distillation zone, and directing a stream of recycled xylene downwardly through said extractive distillation zone, condensing the overhead from such extractive distillation and directing the resulting condensate to a washing zone, recirculating water through the washing zone to provide a molar rate of recycled water which is greater than the molar rate of water in said stream of wet tertiary butyl alcohol, and directing the washed stream to a decanting zone maintained at a temperature within the range from about 50° F. to about 110° F., said decanting zone comprising an upper layer of recyclable xylene and a lower aqueous layer comprising acetone, the recyclable xylene being directed from said decanting zone to an upper portion of said extractive distillation zone;

directing a stream comprising TBA and xylene from the bottom of said extractive distillation zone to a distillation zone designated as a xylene stripping zone, and withdrawing TBA as an overhead stream, and advancing a bottoms stream of xylene as a recyclable xylene stream to a merging zone for combining with the condensate from the overhead from the extractive distillation zone;

directing an aqueous stream comprising acetone from said lower layer of said decantation zone to an acetone stripping distillation zone, from which is withdrawn overhead a stream of acetone, and a bottoms stream from said acetone stripping distillation zone is divided so that a major portion is recirculated to said washing zone for the extraction of acetone into said aqueous layer, and a minor portion is directed to a water stripping distillation zone from the bottom of which is withdrawn a stream of water, and the overhead from which is directed to said decanting zone.

* * * * *